United States Patent [19]

Berger et al.

[11] 4,278,763
[45] Jul. 14, 1981

[54] DIAGNOSTIC AGENTS FOR THE DETECTION OF PROTEOLYTIC ENZYMES

[75] Inventors: Dieter Berger, Viernheim; Franz Braun, Rimbach; Werner Güthlein, Mannheim; Manfred Kuhr, Mannheim; Wolfgang Werner, Mannheim, all of Fed. Rep. of Germany

[73] Assignee: Boehringer Mannheim GmbH, Mannheim-Waldhof, Fed. Rep. of Germany

[21] Appl. No.: 99,180

[22] Filed: Nov. 30, 1979

[30] Foreign Application Priority Data

Dec. 30, 1978 [DE] Fed. Rep. of Germany ....... 2854987

[51] Int. Cl.$^3$ .............................................. C12Q 1/38
[52] U.S. Cl. ...................................... 435/23; 435/24; 23/230 B; 23/932; 252/408; 260/112.5 R
[58] Field of Search ................................... 435/23, 24; 260/112.5 R; 23/230 B, 931, 932; 252/408

[56] References Cited

U.S. PATENT DOCUMENTS

| | | | |
|---|---|---|---|
| 4,061,625 | 12/1977 | Ekenstam et al. ............ | 260/112.5 R |
| 4,063,894 | 12/1977 | Ogawa et al. ...................... | 23/230 B |
| 4,159,979 | 7/1979 | Fujino et al. ................. | 260/112.5 R |
| 4,177,109 | 12/1979 | Tohyama et al. ...................... | 435/24 |
| 4,216,142 | 8/1980 | Ali ...................................... | 435/23 X |

FOREIGN PATENT DOCUMENTS

52-52691 4/1977 Japan .

Primary Examiner—Thomas G. Wyse
Attorney, Agent, or Firm—Sprung, Felfe, Horn, Lynch & Kramer

[57] ABSTRACT

The present invention provides a diagnostic agent for the detection of proteolytic enzymes, comprising an absorbent carrier, a film layer, a powder mixture, a lyophilisate, a solution or a reagent tablet, containing at least one chromogen and an appropriate buffer substance, wherein the chromogen used is an indoxyl- and/or thioindoxyl-amino acid ester and/or peptide ester of the general formula:

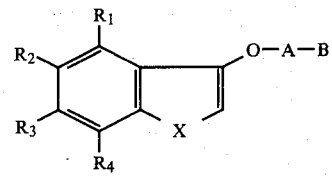

wherein $R_1$, $R_2$, $R_3$ and $R_4$, which can be the same or different, are hydrogen or halogen atoms, lower alkyl, lower alkoxy, aryl, aralkyl, aralkoxy, hydroxyl, carboxy, carboxy lower alkoxy, aralkoxycarbonyl, aralkyloxycarbonyl lower alkoxy, nitro or lower acylamino radicals, whereby two adjacent substituents can also represent an optionally halogenated fused benzene ring, X is a sulphur atom or an imino group optionally substituted by a lower alkyl, aryl, aralkyl or acyl radical, A is an amino acid or peptide residue and B is a nitrogen protective group conventional in peptide chemistry or derived therefrom.

The present invention also provides new compounds of the above-given general formula and processes for the preparation thereof.

Furthermore, the present invention is concerned with the use of the compounds of the above-given general formula for the production of diagnostic agents for the detection of proteolytic enzymes.

28 Claims, No Drawings

DIAGNOSTIC AGENTS FOR THE DETECTION OF PROTEOLYTIC ENZYMES

The present invention is related to diagnostic agents for the detection of proteolytic enzymes. In addition, the invention relates to novel chromogens suitable for use in such diagnostic agents and with processes for the preparation of these chromogens.

The detection of leukocytes in body fluids and especially in urine is outstandingly important in the diagnosis of diseases of the kidney and of the urogenital tract.

Hitherto, this detection has been carried out by the laborious counting of the leukocytes in non-centrifuged urine or in urine sediment.

It is, of course, common to both methods that only intact leukocytes can be counted. On the other hand, it is known that the rate of leukocyte lysis is subject to enormous variations, depending upon the urine medium; thus, for example, in strongly alkaline urines, the leukocytes half life time can be as low as 60 minutes. The result is too low a leukocyte count or even falsely negative findings when the urine samples have been left to stand for a comparatively long time.

Apart from the lysis error, the quantitative microscopic determination of the leukocytes in non-centrifuged, homogenized urine in a counting chamber give quite dependable values. However, in practice, this method is rarely used since it is tiring, laborious and time-consuming and requires the use of trained personnel.

The overwhelming majority of the leukocyte determinations in urine are carried out in medical practice by the so-called viewing field method in the urine sediment. For this purpose, the material to be investigated (sediment) must first be obtained by centrifuging. However, other components of the urine are thereby also enriched, for example salts and epithelial cells, which can make the microscopic counting of the leukocytes considerably more difficult. Varying content of sediment and inhomogeneities of the sediment, as well as, in some cases, differing microscopic enlargement or differing optical equipment of the microscope have the result that the here usual statement regarding the number of leukocytes per microscopic viewing field can involve errors of several hundred percent.

It is, therefore, an object of the present invention to provide a diagnostic agent with which leukocytes present in body fluids can be detected in a manner which is simple and easy to use, as well as as quickly and completely as possible.

One possible detection principle for such a leukocyte test could be an enzymatic reaction, since leukocytes possess a broad spectrum of enzymatic activity.

U.S. Pat. No. 3,087,794 describes a leukocyte determination method which is carried out via the peroxidate activity present in the granular leukocytes (granulocytes). An absorbent carrier which is impregnated with hydrogen peroxide and an organic indicator, for example o-tolidine, indicates the presence of leukocytes by the formation of a colored oxidation product. However, such a test suffers from serious disadvantages: on the one hand, peroxidate reactions using o-tolidine, possess, quite generally, a considerable tendency to be disturbed by reducing substances present in urine, for example ascorbic acid. Furthermore, there are numerous literature references (see, for example, L. Mettler, Med. Welt, 23, 399/1972) to the instability of leukocyte peroxidase in the urine medium, which gives rise to falsely negative findings. Even more serious is the expected poor selectively of this test with regard to erythrocytes.

For some years, in histo- and cytochemical enzymology, detection methods have found a firm place which depends upon the esterolytic activity of the enzymes present in the systems to be determined (cf., for example, A. G. E. Pearse, Histochemistry, Theoretical and Applied). In principle, colorless and pale colored esters are employed which, by means of enzymatic fission, mostly break down into a colorless acid component and into an also colorless alcohol or phenol component. The latter is then reacted, in a reaction following the enzymatic saponification, to give colored products, for example by coupling with diazonium salts or oxidative reactions.

Thus, for example, in Klin. Wschr., 46, 642/1968, F. Schmalzl and H. Braunsteiner describe a specific cytochemical leukocyte esterase detection with naphthol-AS-D-chloroacetate as substrate and a diazonium salt for the formation of a colored azo compound.

For a diagnostic agent for the rapid and simple detection of leukocytes in body fluids, for example in urine, two-component systems of this type have not proved to be suitable since, as is known, many compounds occurring in urine, for example, urobilinogen, stercobilinogen, bilirubin and the like, react with diazonium salts. Furthermore, this detection method is much too insensitive. For example, samples containing 5000 leukocytes/$\mu$l. do not show any reaction.

British Patent Specification No. 1,128,371 describes a diagnostic agent for the detection of hydrolytic enzymes in body fluids. In this case, an absorbent carrier is impregnated with colorless indoxyl or thioindoxyl esters and possibly with a buffer and an oxidation agent. When hydrolytic enzymes are present, the esters are split to give free indoxyl or free thioindoxyl, from which, by the action of atmospheric oxygen or of an oxidation agent, deep-colored indigo or thioindigo is formed. The compounds disclosed in this British Patent cannot be used for a leukocyte test since even with 10,000 leukocytes/$\mu$l. they do not show any reaction.

Thus, even today, no test strips are commercially available which permit a simple and rapid detection of leukocytes, even though the detection of leukocytes in urine is one of the most frequently performed clinical investigations.

Surprisingly, we have now found stable and rapidly indicating diagnostic agents with which leukocytes can be readily detected in body fluid when, as a substrate for the detection of the esterases (proteases) present in the neutrophilic leukocyte granulocytes, there are used indoxyl or thioindoxyl-amino acid esters or peptide esters. Furthermore, we have found that these substrates are also excellent for the general detection of proteolytic enzymes, for example of elastase, chymotrypsin and trypsin, in purely aqueous solutions and also in body fluids, for example in plasma, serum, liquor, pancreatic secretions and aqueous extracts of faeces.

The present invention, provides a diagnostic agent for the detection of proteolytic enzymes and especially for the detection of proteases present in leukocytes in body fluids, comprising an absorbent carrier, a film layer, a powder mixture, a lyophilizate, a solution or a reagent tablet containing at least one chromogen and conventional additives, wherein the chromogen used is an indoxyl- and/or thioindoxyl-amino acid ester and/or peptide ester of the formula:

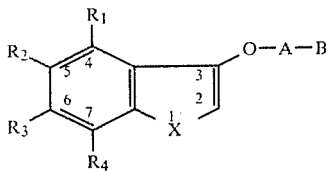

(I)

wherein $R_1$, $R_2$, $R_3$ and $R_4$, which can be the same or different, are hydrogen or halogen atoms, lower alkyl, lower alkoxy, aryl, aralkyl, aralkoxy, hydroxyl, carboxy, carboxy lower alkoxy, aralkoxycarbonyl, aralkoxycarbonyl lower alkoxy, nitro or lower acylamino radicals or whereby two adjacent substituents can together represent an optionally halogen-substituted fused benzene ring, X is a sulphur atom or an imino group optionally substituted by a lower alkyl, aryl, aralkyl or acyl radical, A is an amino acid or peptide residue and B is a nitrogen protective group conventional in peptide chemistry or derived therefrom.

The present invention is also concerned with the use of indoxyl- and/or thioindoxyl-amino acid esters and/or peptides esters of general formula (I) for the production of diagnostic agents for the detection of proteolytic enzymes, especially of proteases present in leukocytes in body fluids.

All of the indoxyl- and thioindoxyl-amino acid esters and peptide esters of general formula (I) are new compounds.

Therefore, the present invention also provides the indoxyl- and thioindoxyl-amino acid esters and peptide esters of general formula (I), as well as processes for the preparation thereof.

The new indoxyl- and thioindoxyl-amino acid esters and peptide esters of general formula (I) can be prepared by methods which are known from peptide chemistry.

Preferably, the corresponding indoxyl or thioindoxyl compounds of the general formula:

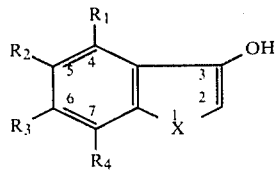

(II)

wherein $R_1$, $R_2$, $R_3$, $R_4$ and X have the same meanings as above, are reacted in known manner with amino acids or peptides of the general formula:

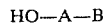    (III)

wherein A and B have the same meanings as above, or with appropriate reactive derivatives thereof.

As reactive derivatives, there can be used, for example, the acid chlorides or the mixed anhydrides conventionally employed in peptide syntheses, for example those with ethyl chloroformate, or active esters.

The indoxyl or thioindoxyl compounds of general formula (II), as well as the amino acids and peptides of general formula (III), are either known compounds (cf., for example, P. Friedlaender, Fortschritte der Teerfarbenfabrikation and verwandter Industriezweige, Vol.3-20 and Houben-Weyl, Methoden der organischen Chemie, Vol.15/1), or can be prepared analogously to known compounds.

By halogen in the definitions of $R_1$, $R_2$, $R_3$ and $R_4$, there is to be understood fluorine, chlorine, bromine and iodine, chlorine and bromine being preferred.

The lower alkoxy radical in the definition of $R_1$, $R_2$, $R_3$ and $R_4$, as well as the lower alkyl radical in the definition of $R_1$, $R_2$, $R_3$, $R_4$ and X, contain up to 5 and preferably up to 3 carbon atoms, the methoxy and methyl radicals being especially preferred.

By an aralkoxy radical in the definition of $R_1$, $R_2$, $R_3$ and $R_4$, as well as an aralkyl radical in the definition of $R_1$, $R_2$, $R_3$, $R_4$ and X, there are to be understood, for example, phenyl and naphthyl radicals substituted by oxy lower alkyl or lower alkyl radicals, respectively, the alkyl moieties thereby containing up to 5 and preferably up to 3 carbon atoms. The benzyloxy and benzyl radicals are especially preferred.

The lower acylamino radicals in the definitions of $R_1$, $R_2$, $R_3$ and $R_4$ are the amide groupings of aliphatic carboxylic acids containing up to 5 and preferably up to 3 carbon atoms. The acetylamino radical is especially preferred.

The acyl radical in the definition of X is the residue of an aliphatic carboxylic acid containing up to 5 and preferably up to 3 carbon atoms or of an aromatic carboxylic acid, for example of benzoic acid or of a naphthoic acid. The acetyl and benzoyl radicals are especially preferred.

By an aryl radical in the definition of $R_1$, $R_2$, $R_3$, $R_4$ and X there are preferably to be understood the phenyl and naphthyl radicals.

The amino acid residue in the definition of A is preferably a residue of one of the naturally-occurring amino acids in the L- or D-form or also in the racemic form. The residues of glycine, alanine, valine, leucine, isoleucine, phenylalanine and tyrosine are especially preferred. Any free hydroxyl groups possibly present can be acylated and preferably acetylated.

By a peptide residue in the definition of A, there is to be understood, for example, a di-, tri-, tetra- or pentapeptide and preferably a di- or tripeptide, whereby, as amino acid components, the above-mentioned amino acids are preferably used.

The nitrogen protective group conventional in peptide chemistry used in the definition of B can be, for example, an acyl, oxycarbonyl, thiocarbonyl, sulphonyl, sulphenyl, vinyl, cyclohexenyl, phosphoryl or carbamoyl group.

The indoxyl- or thioindoxyl-amino acid esters and peptide esters of general formula (I) employed as chromogens according to the present invention are usually employed in concentrations of from $10^{-4}$ to 1 mol/liter and preferably of $10^{-3}$ to $10^{-1}$ mol/liter of impregnation solution, coating mass or fluid to be investigated.

A further component of the diagnostic agent for the detection of proteolytic enzymes and especially of leukocyte proteases is an appropriate buffer system. For this purpose, there can be used, for example, a phosphate, borate, barbiturate, tris-(hydroxymethyl)aminomethane (tris), 2-amino-2-methyl-propane-1,3-diol (amediol) or amino acid buffer. The pH value and the capacity of the buffer must be so chosen that, in the measurement solution or on the test strip, there is obtained a pH value of from 6 to 10 and preferably of from 7 to 9.

Furthermore, in the production of the diagnostic agent according to the present invention for the detection of proteolytic enzymes and especially of leukocyte proteases in body fluids, oxidation agents can additionally be employed in order to react the indoxyl or the thioindoxyl compounds initially formed by the enzymatic reaction to give colored indigo or thioindigo substances. These oxidation agents, for example potassium hexacyanoferrate-III, potassium bromate, potassium chromate, phenazine methosulphate or tetrazolium salts, can be used in concentrations of from $10^{-4}$ to 1 mol/liter and preferably of $10^{-3}$ to $10^{-1}$ mol/liter of impregnation solution, coating mass or fluid to be investigated.

A further component of a diagnostic agent for the detection of proteolytic enzymes and especially of leukocyte proteases can be a wetting agent since a somewhat shortened reaction time and, in some cases, a more brilliant color can thereby be achieved. It is preferable to use non-ionogenic wetting agents but amphoteric, cation- and anion-active wetting agents can also be used. The concentration of the wetting agent can be 0.05 to 2% and preferably 0.1 to 1%.

The agent according to the present invention can be produced, for example, by impregnating an absorbent carrier, preferably filter paper, cellulose or synthetic fibre fleeces, with solutions of the necessary reagents usually employed for the production of test strips, for example substrate, buffer, optionally wetting agent, oxidation agent, etc., in readily volatile solvents, for example water, methanol, ethanol or acetone. Impregnation is preferably carried out in two separate steps: impregnation is first carried out with an aqueous solution which contains the buffer and other water-soluble additives. Thereafter, impregnation is carried out with a solution of a protease substrate of general formula (I). In special cases, the sequence of impregnation can also be reversed. The finished test papers can be used as such or stuck in known manner on to handles or preferably sealed between synthetic resins and fine-meshed materials in the manner described in Federal Republic of Germany Patent Specification No. 21 18 455.

For the production of film-coated test strips, all the reagents are introduced into and homogeneously mixed with a solution or dispersion of a film-forming substance, for example a polyvinyl ester or a polyamide, whereafter the mixture is applied in a thin layer on to a synthetic resin carrier and dried. The film-coated test strips according to the present invention are, after drying, cut up and can be used as such or stuck in known manner on to handles or, for example, sealed between synthetic resins and fine-meshed materials in the manner described in German Patent Specification No. 21 18 455.

The diagnostic agent according to the present invention for the detection of proteolytic enzymes and especially of leukocyte proteases in the form of powder mixtures or reagent tablets can be produced by mixing the above-mentioned components of the test with conventional galenical additives and granulated. Additives of this type include, for example, carbohydrates, such as mono-, oligo- and polysaccharides, or sugar alcohols, such as mannitol, sorbitol or xylitol, or other soluble inert compounds, such as polyethylene glycols or polyvinylpyrrolidones. The powder mixture or reagent tablets generally have a final weight of about 50 to 200 mg. and preferably of 50 to 80 mg.

For the production of lyophilizates with a total weight of, in each case, 5 to 20 mg. and preferably of about 10 mg., a solution is freeze-dried which, besides all of the reagents needed for the test, contains conventional structural formers, for example polyvinylpyrrolidinones, and possibly further filling materials, for example mannitol, sorbitol or xylitol.

The diagnostic agent according to the present invention in the form of a solution preferably contains all of the reagents needed for the test. As solvents, there can be used water or mixtures of water with a water-soluble organic solvent, for example methanol, ethanol, acetone or dimethylformamide. For reasons of storage stability, it can be advantageous to divide the reagents needed for the test into two or more solutions which are first mixed together at the time of carrying out the actual investigation.

The diagnostic agents thus produced make it possible, after dipping into or after adding the body fluid in question, rapidly and simply to detect the presence of proteolytic enzymes by means of a color formation which can be assessed visually or photometrically, for example by remission photometry or in a cuvette. Since the activity of the leukocyte proteases per cell can be regarded as being approximately constant, the leukocyte concentration of the investigated body fluid can be determined from the intensity of the color formation. In this way, with the diagnostic agent according to the present invention, there can be determined not only intact but also lysed leukocytes since the activity of the leukocyte proteases is fully maintained even after lysis of the leukocytes. Consequently, errors due to lysis do not occur.

The following Examples are given for the purpose of illustrating the present invention:

EXAMPLE 1

Filter paper (for example Schleicher & Schül 23 SL) is successively impregnated with the following solutions and then dried at 60° C.

Solution 1 disodium tetraborate decahydrate, 1.91 g.
distilled water, about 30 ml.
adjust the solution with 0.1 N hydrochloric acid to a pH value of 8.0
distilled water, ad 100.0 ml.

Solution 2

3-[N-(benzyloxycarbonyl)-L-alanyloxy]-indole, 33.8 mg.
acetone, ad 100.0 ml.

A colorless test paper is obtained which, upon dipping into a leukocyte-containing urine, becomes bright turquoise to blue colored, depending upon the leukocyte concentration. The following leukocyte concentrations can be determined:

5000 leukocytes/µl. urine in about 2 minutes
1000 leukocytes/µl. urine in about 6 minutes
500 leukocytes/µl. urine in about 10 minutes
200 leukocytes/µl. urine in about 15 minutes.

The sensitivity of the test lies at about 200 leukocytes/µl. The assessment can also be carried out by remission photometry at 620 nm.

Test papers with similar properties (sensitivities: 200 to 2000 leukocytes/µl.) are obtained when, instead of 3-[N-(benzyloxycarbonyl)-L-alanyloxy]-indole, the following substrates are used; when not otherwise mentioned, there are also obtained bright turquoise to blue colorations of the colorless test papers upon dipping into leukocyte-containing samples:

1.1. 3-[N-(Benzyloxycarbonyl)-L-alanyloxy]-4-methylindole
1.2. 3-[N-(Benzyloxycarbonyl)-L-alanyloxy]-5-methylindole
1.3. 3-[N-(Benzyloxycarbonyl)-L-alanyloxy]-6-methylindole
1.4. 3-[N-(Benzyloxycarbonyl)-L-alanyloxy]-7-methylindole
1.5. 3-[N-(Benzyloxycarbonyl)-L-alanyloxy]-4,7-dimethylindole
1.6. 3-[N-(Benzyloxycarbonyl)-L-alanyloxy]-4-chloroindole
1.7. 3-[N-(Benzyloxycarbonyl)-L-alanyloxy]-5-bromoindole
1.8. 3-[N-(Benzyloxycarbonyl)-L-alanyloxy]-6-chloroindole coloration: colorless to purple
1.9. 3-[N-(Toluene-4'-sulphonyl)-L-alanyloxy]-4-chloro-5-bromoindole
1.10. 3-[N-(Toluene-4'-sulphonyl)-L-alanyloxy]-4,5,7-trichloroindole
1.11. 3-[N-(Toluene-4'-sulphonyl)-L-alanyloxy]-4-chloro-5-bromo-7-methyl-indole
1.12. 3-[N-(Toluene-4'-sulphonyl)-L-alanyloxy]-5-hydroxyindole
1.13. 3-[N-(Benzyloxycarbonyl)-L-alanyloxy]-5-methoxyindole
1.14. 3-[N-(Toluene-4'-sulphonyl)-L-alanyloxy]-5-benzyloxyindole
1.15. 3-[N-(Toluene-4'-sulphonyl)-L-alanyloxy]-4-carboxyindole
1.16. 3-[N-(Toluene-4'-sulphonyl)-L-alanyloxy]-4-benzyloxycarbonyl-indole
1.17. 3-[N-(Toluene-4'-sulphonyl)-L-alanyloxy]-5-(carboxymethoxy)-indole
1.18. 3-[N-(Toluene-4'-sulphonyl)-L-alanyloxy]-5-(benzyloxycarbonyl-methoxy)indole
1.19. 3-[N-(Toluene-4'-sulphonyl)-L-alanyloxy]-6-nitroindole
1.20. 3-[N-(Toluene-4'-sulphonyl)-L-alanyloxy]-6-acetylaminoindole
1.21. 3-[N-(Toluene-4'-sulphonyl)-L-alanyloxy]-benzo[g]-indole.
coloration: colorless to green
1.22. 1-Methyl-3-[N-(benzyloxycarbonyl)-L-alanyloxy]-indole
coloration: colorless to green
1.23. 1-Benzyl-3-[N-(toluene-4'-sulphonyl)-L-alanyloxy]-indole
coloration: colorless to green
1.24. 1-Phenyl-3-[N-(toluene-4'-sulphonyl)-L-alanyloxy]-indole
coloration: colorless to blue-green
1.25. 1-Acetyl-3-[N-(toluene-4'-sulphonyl)-L-alanyloxy]-indole
coloration: colorless to red
1.26. 1-Benzoyl-3-[N-(toluene-4'-sulphonyl)-L-alanyloxy]-indole
coloration: colorless to violet
1.27. 3-[N-(Benzyloxycarbonyl)-glycyloxy]-indole
1.28. 3-[N-(Toluene-4'-sulphonyl)-glycyloxy]-indole
1.29. 3-[N-(Toluene-2'-sulphonyl)-L-alanyloxy]-indole
1.30. 3-[N-(Toluene-3'-sulphonyl)-L-alanyloxy]-indole
1.31. 3-[N-(Toluene-4'-sulphonyl)-L-alanyloxy]-indole
1.32. 3-[N-(Toluene-4'-sulphonyl)-D-alanyloxy]-indole
1.33. 3-[N-(Benzyloxycarbonyl)-D,L-alanyloxy]-indole
1.34. 3-[N-(Benzyloxycarbonyl)-L-valyloxy]-indole
1.35. 3-[N-(Toluene-4'-sulphonyl)-L-valyloxy]-indole
1.36. 3-[N-(Benzyloxycarbonyl)-L-leucyloxy]-indole
1.37. 3-[N-(Benzyloxycarbonyl)-L-isoleucyloxy]-indole
1.38. 3-[N-(Benzyloxycarbonyl)-L-phenylalanyloxy]-indole
1.39. 3-[N-(Toluene-4'-sulphonyl)-L-phenylalanyloxy]-indole
1.40. 3-[N-Acetyl-L-tyrosyloxy]-indole
1.41. 3-[N-Benzoyl-L-tyrosyloxy]-indole
1.42. 3-[N-(Benzyloxycarbonyl)-L-tyrosyloxy]-indole
1.43. 3-[N-(Toluene-4'-sulphonyl)-L-tyrosyloxy]-indole
1.44. 3-[N-(Toluene-4'-sulphonyl)-O-acetyl-L-tyrosyloxy]-indole
1.45. 3-[N-(Benzyloxycarbonyl)-L-alanyl-L-alanyloxy]-indole
1.46. 3-[N-(Toluene-4'-sulphonyl)-D-alanyl-L-alanyloxy]-indole
1.47. 3-[N-(Benzyloxycarbonyl)-L-alanyl-L-alanyl-L-alanyloxy]-indole
1.48. 3-[N-(Toluene-4'-sulphonyl)-D-alanyl-D-alanyl-L-alanyloxy]-indole
1.49. 3-[N-Formyl-L-alanyloxy]-indole
1.50. 3-[N-Acetyl-L-alanyloxy]-indole
1.51. 3-[N-Succinyl-L-alanyloxy]-indole
1.52. 3-[N-Benzoyl-D,L-alanyloxy]-indole
1.53. 3-[N-Phthaloyl-L-alanyloxy]-indole
1.54. 3-[N-(Ethoxycarbonyl)-L-alanyloxy]-indole
1.55. 3-[N-(test.-Butyloxycarbonyl)-L-alanyloxy]-indole
1.56. 3-[N-(3',6'-Dioxa-n-heptyloxycarbonyl)-L-alanyloxy]-indole
1.57. 3-[N-(Cyclohexyloxycarbonyl)-L-alanyloxy]-indole
1.58. 3-N-(Phenyloxycarbonyl)-L-alanyloxy]-indole
1.59. 3-[N-(4'-Methylbenzyloxycarbonyl)-L-alanyloxy]-indole
1.60. 3-[N-(4'-Methoxybenzyloxycarbonyl)-L-alanyloxy]-indole
1.61. 3-[N-(4'-Nitrobenzyloxycarbonyl)-L-alanyloxy]-indole
1.62. 3-[N-(N'-Piperidino-oxycarbonyl)-L-alanyloxyl-indole
1.63. 3-[N-(Furyl-[2']-methoxycarbonyl)-L-alanyloxy]-indole
1.64. 3-[N-(Thienyl-[2']-methoxycarbonyl)-L-alanyloxy]-indole
1.65. 3-[N-(Benzylthiocarbonyl)-L-alanyloxy]-indole
1.66. 3-[N-(Methansulphonyl)-L-alanyloxy]-indole
1.67. 3-[N-(Benzylsulphonyl)-L-alanyloxy]-indole
1.68. 3-[N-(Benzenesulphonyl)-L-alanyloxy]-indole
1.69. 3-[N-(4'-Bromobenzenesulphonyl)-L-alanyloxy]-indole
1.70. 3-[N-(4'-Nitrobenzenesulphonyl)-L-alanyloxy]-indole
1.71. 3-[N-(4'-Dimethylaminobenzenesulphonyl)-L-alanyloxy]-indole
1.72. 3-[N-(4'-Acetylaminobenzenesulphonyl)-L-alanyloxy]-indole
1.73. 3-[N-(4'-n-Butyl-benzenesulphonyl)-L-alanyloxy]-indole
1.74. 3-[N-(4'-tert.-Butyl-benzenesulphonyl)-L-alanyloxy]-indole
1.75. 3-[N-(4'-n-Octyl-benzenesulphonyl)-L-alanyloxy]-indole
1.76. 3-[N-(4'-Hydroxybenzenesulphonyl)-L-alanyloxy]-indole
1.77. 3-[N-(4'-Methoxybenzenesulphonyl)-L-alanyloxy]-indole
1.78. 3-[N-(4'-Benzyloxybenzenesulphonyl)-L-alanyloxy]-indole 1.79. 3-[N-(4'-(2"-Hydroxyethoxy)-benzenesulphonyl)-L-alanyloxy]-indole
1.80. 3-[N-(4'-(3"-Oxa-5"-hydroxy-n-pentyloxy)-benzenesulphonyl)-L-alanyloxy]-indole
1.81. 3-[N-(4'-(3",6"-Dioxa-n-heptyloxy)-benzenesulphonyl)-L-alanyloxy]-indole
1.82. 3-[N-(4'-(2"-Hydroxyethyl)-benzenesulphonyl)-L-alanyloxy]-indole
1.83. 3-[N-(4'-{2"-{{4"'-Nitrobenzyloxy}}-ethyl}-benzenesulphonyl)-L-alanyloxy]-indole
1.84. 3-[N-(4'-(2"-Chloroethyl)-benzenesulphonyl)-L-alanyloxy]-indole
1.85. 3-[N-(4'-Acetylbenzenesulphonyl)-L-alanyloxy]-indole
1.86. 3-[N-(4'-Cyanobenzenesulphonyl)-L-alanyloxy]-indole
1.87. 3-[N-(4'-Carboxybenzenesulphonyl)-L-alanyloxy]-indole
1.88. 3-[N-(4'-Methoxycarbonylbenzenesulphonyl)-L-alanyloxy]-indole
1.89. 3-[N-(4'-Benzyloxycarbonylbenzenesulphonyl)-L-alanyloxy]-indole
1.90. 3-[N-(4'-Carbamoylbenzenesulphonyl)-L-alanyloxy]-indole
1.91. 3-[N-(4'-{Dimethylcarbamoyl}-benzenesulphonyl)-L-alanyloxy]-indole
1.92. 3-[N-(4'-Carboxymethylbenzenesulphonyl)-L-alanyloxy]-indole
1.93. 3-[N-(4'-Carboxymethoxybenzenesulphonyl)-L-alanyloxy]-indole
1.94. 3-[N-(4'-Carboxymethylaminobenzenesulphonyl)-L-alanyloxy]-indole
1.95. 3-[N-(4'-{Benzyloxycarbonylmethylamino}-benzenesulphonyl)-L-alanyloxy]-indole
1.96. 3-[N-(4'-Fluorobenzenesulphonyl)-L-alanyloxy]-indole
1.97. 3-[N-(4'-Fluorosulphonyl-benzenesulphonyl)-L-alanyloxy]-indole
1.98. 3-N-(4'-Sulphamoylbenzenesulphonyl)-L-alanyloxy]-indole
1.99. 3-[N-Methyl-N-(toluene-4'-sulphonyl)-L-alanyloxy]-indole
1.100. 3-[N-Acetyl-N-(toluene-4'-sulphonyl)-L-alanyloxy]-indole
1.101. 3-[N-(2',4',6'-Trimethylbenzenesulphonyl)-L-alanyloxy]-indole
1.102. 3-[N-(Biphenyl-4'-sulphonyl)-L-alanyloxy]-indole
1.103. 3-[N-(Naphthalene-2'-sulphonyl)-L-alanyloxy]-indole
1.104. 3-[N-(4'-Acetylaminonaphthalin-1'-sulphonyl)-L-alanyloxy]-indole
1.105. 3-[N-(5'-Dimethylaminonaphthalene-1'-sulphonyl)-L-alanyloxy]-indole
1.106. 3-[N-(Quinoline-8'-sulphonyl)-L-alanyloxy]-indole
1.107. 3-[N-(Pyridine-3'-sulphonyl)-L-alanyloxy]-indole
1.108. 3-[N-(2'-Nitrobenzenesulphenyl)-L-alanyloxy]-indole coloration: yellow to green
1.109. 3-[N-(1'-Methyl-2'-benzoylvinyl)-L-alanyloxy]-indole
1.110. 3-[N-(5',5'-Dimethyl-3'-oxocyclohexen-1'-yl)-L-alanyloxy]-indole
1.111. 3-[N-(Diphenylcarbamoyl)-L-alanyloxy]-indole
1.112. 3-[N-(Di-{4'-nitrobenzyl}-phosphoryl)-L-alanyloxy]-indole
1.113. 3-[N-(Di-{4'-bromobenzyl}-phosphoryl)-L-alanyloxy]-indole
1.114. 3-[N-(Toluene-4'-sulphonyl)-L-alanyloxy]-5-benzyl-indole
1.115. 3-[N-(Toluene-4'-sulphonyl)-L-alanyloxy]-5-phenyl-indole
1.116. 3-[N-(Toluene-4'-sulphonyl)-L-alanyloxy]-5-methoxy-indole

EXAMPLE 2

Filter paper (for example Schleicher & Schüll 23 SL) is successively impregnated with the following solutions and then dried at 60° C.:

Solution 1 tris-(hydroxymethyl)-aminomethane, 0.61 g.
potassium hexacyanoferrate III, 32.9 mg.
distilled water, about 30 ml. adjust the solution with 0.1 N hydrochloric acid to a pH value of 8.0
distilled water, ad 100. 0 ml.

Solution 2

3-[N-(benzyloxycarbonyl)-L-alanyloxy]-benzo-[b]-thiophene, 35.5 mg.
acetone, ad 100.0 ml.

A yellow- colored test paper is obtained which, upon dipping into leukocyte-containing urines, becomes red colored.

The sensitivity of the test lies at about 1000 leukocytes/µl. urine.

The evaluation can be carried out by remission photometry at 576 nm.

With the substrates mentioned in Example 1 and with oxidation agents, for example the above-mentioned potassium hexacyanoferrate III, or with, for example, potassium bromate, potassium chromate, phenazine methosulphate or tetrazolium salts, test papers are obtained which, in comparison with analogous test papers without oxidation agents, show, in some cases, slightly shortened reaction times.

EXAMPLE 3

Filter paper (for example Schleicher & Schül 23 SL) is successively impregnated with the following solutions and then dried at 60° C.:

Solution 1 disodium tetraborate decahydrate, 1.91 g.
distilled water, about 30 ml.
nonylphenol polyglycol ether, 0.2 g.
adjust the solution with 0.1 N hydrochloric acid to a pH value of 8.0
distilled water ad 100.0 ml.

Solution 2

3-[N-(benzyloxycarbonyl)-L-alanyloxy]-indole, 33.8 mg. acetone, ad 100.0 ml.

A colourless test paper is obtained which, upon dipping into a leukocyte-containing urine, becomes bright turquoise to blue colored depending upon the leukocyte concentration. In comparison with the formulation according to Example 1, there are obtained somewhat shortened reaction times and slightly more brilliant colors.

Also with the other substrates of Examples 1 and 2, together with wetting agents, for example the above-mentioned nonylphenyl polyglycol ether (non-ionic) but also with, for example, coconut imidazoline compounds (amphoteric) or benzyltrimethylammonium chloride (cation-active) or sodium sulphonatododecylbenzene (anion-active), test papers are obtained which, in comparison with analogous test papers without a wetting agent, show, in some cases, slightly shortened reaction times and somewhat more brilliant colors.

EXAMPLE 4

Solution 1.

3-[N-benzoyl-D,L-alanyloxy]-indole, 154.2 mg.
methanol, ad 100.0 ml.

Solution 2 disodium tetraborate decahydrate, 7.63 g.
distilled water, about 50 ml.
adjust the solution with 1 N hydrochloric acid to a pH value of 8.0
distilled water, ad 100.0 ml.

The following are mixed in a test tube:
1 ml. Solution 1
1 ml. Solution 2
2 ml. leukocyte-containing urine The mixture gradually becomes bright green to deep blue colored, depending upon the leukocyte concentration.

After standing for about 10 minutes at ambient temperature, the leukocyte concentration is determined visually with the help of comparison colors or photometrically, for example in a 1 cm. cuvette at 620 nm.

The sensitivity of the test lies at about 200 leukocytes/$\mu$l. urine.

Also with the other substrates of Examples 1 and 2, test tube and cuvette tests can be carried out with similar sensitivities (200 to 1000 leukocytes/$\mu$l. urine).

EXAMPLE 5

A tablet containing:
3-[N-(4'-carboxymethylaminobenzenesulphonyl)-L-alanyloxy]-indole, 2.0 mg.
potassium dihydrogen phosphate, 0.8 mg.
disodium hydrogen phosphate, 16.8 mg. dihydrate,
mannitol, ad 70.0 mg.
is introduced into 2 ml. of a leukocyte-containing urine in a test tube. The urine gradually becomes bright green to deep blue colored, depending upon the leukocyte concentration.

After standing for 10 minutes at ambient temperature, the leukocyte concentration is determined visually with the help of comparison colors or photometrically, for example in a 1 cm. microcuvette at 620 nm.

The sensitivity of the test lies at about 200 leukocytes/$\mu$l. of urine. The reaction time can be considerably shortened when the incubation is carried out at 37° C.

With the other substrates of Examples 1 and 2, similar sensitivities (200 to 1000 leukocytes/$\mu$l.) can be achieved. In the case of sparingly soluble substrates, the addition of an organic solvent, for example methanol or dimethylformamide, is recommended.

EXAMPLE 6

Filter paper (for example Schleicher & Schüll 23 SL) is successively impregnated with the following solutions and then dried at 60° C.:

Solution 1 disodium tetraborate decahydrate, 1.91 g.
distilled water, about 30 ml.
adjust the solution with 0.1 N hydrochloric acid to a pH value 8.0.
distilled water, ad 100.0 ml.

Solution 2

3-[N-(toluene-4'-sulphonyl)-L-tyrosyloxy]-indole, 45.1 mg.
acetone, ad 100.0 ml.

A colorless test paper is obtained which, upon dipping into aqueous solutions which contain the proteolytic enzyme chymotrypsin, become blue colored. In this manner, even concentrations of 0.02 U chymotrypsin per ml. can still be detected in about 6 to 7 minutes.

(The stated enzyme activity was determined with N-acetyl-L-tyrosine ethyl ester as substrate at 25° C., pH 7.0 and $\lambda = 237$ nm.).

Also with the other substrates of Examples 1 and 2, depending upon the amino acid or peptide residue, chymotrypsin or other proteolytic enzymes, for example elastase or trypsin, can be detected in purely aqueous solutions or also, for example, in body fluids, for example whole blood, serum, liquor, pancreatic secretion or aqueous faecal extracts.

EXAMPLE 7

3-[N-(Toluene-4'-sulphonyl)-L-alanyloxy]-indole

Solution 1

For the preparation of the acid chloride by the one-step method, 5.35 g. (0.022 mol) N-(toluene-4-sulphonyl)-L-alanine are dissolved in 20 ml. anhydrous dimethylformamide (DMF) and cooled to $-30°$ C. Then, while stirring and cooling, 1.76 ml. (0.024 mol) thionyl chloride is pipetted thereto and the reaction mixture left to stand for 30 minutes in a cold bath at $-30°$ C.

Solution 2

By means of a weak current of nitrogen, the air is completely removed from a 250 ml. three-necked flask equipped with a stirrer, thermometer and a gas inlet and outlet, whereafter a solution of 2.90 g. (0.022 mol) indoxyl(3-hydroxyindole) in 40 ml. anhydrous DMF is introduced, followed by the addition of 9.74 ml. anhydrous pyridine, whereafter the mixture is cooled to $-15°$ C.

Reaction

Solution 1 is poured into solution 2 and the reaction mixture stirred, with the exclusion of oxygen and water, for about 5 hours at $-15°$ C. until indoxyl can no longer be detected by thin layer chromatography.

For working up, the reaction mixture is concentrated in a vacuum at a bath temperature of 40° to 50° C. The residue obtained is taken up in 100 ml. ethyl acetate and successively washed twice with 30 ml. amounts of 1 N aqueous citric acid, 20 ml. water, 50 ml. 5% aqueous sodium bicarbonate solution and 25 ml. water. The ethyl acetate phase is dried with anhydrous sodium sulphate and evaporated in a vacuum. The crude product thus obtained is purified by column chromatography using silica gel and a mixture of toluene and dioxan (9:1 v/v). After distilling off in a vacuum the solvent from the collected fractions, the residue is stirred with diethyl ether to give 1.45 g. (18.4% of theory) 3-[N-(toluene-4'-sulphonyl)-L-alanyloxy]-indole in the form of colorless crystals: m.p. 103° C.; $[\alpha]_D^{20} = -56.6°$ (C=1% in methanol).

As by-product, from the other fractions of the above-mentioned column chromatographic separation there can also be isolated 0.89 g. (11.3% of theory) 1-[N-(toluene-4'-sulphonyl)-L-alanyloxy]-3-hydroxyindole (=1-[N-(toluene-4'-sulphonyl)-L-alanyloxy]-3-oxoindoline which, after recrystallization from ethyl acetate, is obtained in the form of colorless crystals; m.p. 187°-188° C.; $[\alpha]_D^{20} = -41.7°$ (C=1% in DMF).

In an analogous manner, by the reaction of the appropriately substituted indoxyl compounds with the appropriate amino acids, the following substrates can also be prepared; in all cases (except 7.23 to 7.27), as by-products there are obtained, the above mentioned 1-substituted 3-hydroxyindoles:

7.1. 3-[N-(Benzyloxycarbonyl)-L-alanyloxy]-indole
colorless crystals; m.p. 123° C., $[\alpha]_D^{20} = -49.0°$ c=1% (methanol)

7.2. 3-[N-(Benzyloxycarbonyl)-L-alanyloxy]-4-methylindole
colorless crystals; m.p. 113° C., $[\alpha]_D^{20} = -44.6°$ c=1% (methanol)

7.3. 3-[N-(Benzyloxycarbonyl)-L-alanyloxy]-5-methylindole
colorless crystals; m.p. 143°-144° C., $[\alpha]_D^{20} = -48.2°$, c=1% (methanol)

7.4. 3-[N-(Benzyloxycarbonyl)-L-alanyloxy]-6-methylindole
colorless crystals; m.p. 148° C. $[\alpha]_D^{20} = -49.0°$, c=1% (methanol)

7.5. 3-[N-(Benzyloxycarbonyl)-L-alanyloxy]-7-methylindole
colorless crystals; m.p. 146° C. $[\alpha]_D^{20} = -51.2°$, c=1% (methanol)

7.6. 3-[N-(Benzyloxycarbonyl)-L-alanyloxy]-4,7-dimethylindole
colorless crystals; m.p. 121° C. $[\alpha]_D^{20} = -46.3°$, c=1% (methanol)

7.7. 3-[N-(Benzyloxycarbonyl)-L-alanyloxy]-4-chloroindole
colorless crystals; m.p. 142°-143° C. $[\alpha]_D^{20} = -61.4°$, c=1% (methanol)

7.8. 3-[N-(Benzyloxycarbonyl)-L-alanyloxy]-5-bromoindole.
colorless crystals; m.p. 138° C. $[\alpha]_D^{20} = -28.0°$, c=1% (methanol)

7.9. 3-[N-(Benzyloxycarbonyl)-L-alanyloxy]-6-chloroindole
colorless crystals; m.p. 170° C. $[\alpha]_D^{20} = -41.3°$, c=1% (methanol)

7.10. 3-[N-(Toluene-4'-sulphonyl)-L-alanyloxy]-4-chloro-5-bromoindole
colorless crystals, m.p. 150°-152° C. $[\alpha]_D^{20} = -31.0°$, c=1% (methanol)

7.11. 3-[N-Toluene-4'-sulphonyl)-L-alanyloxy]-4,5,7-trichloroindole 7.12. 3-[N-(Toluene-4'-sulphonyl)-L-alanyloxy]-4-chloro-5-bromo-7-methyl-indole
pale beige colored crystals; m.p. 143°-145° C., TLC: finished plate silica gel (elution agent: toluene-dioxan 2:1 v/v), detection: UV, NH$_3$ (gas), R$_F$ value: 0.56)

7.13. 3-[N-(Toluene-4'-sulphonyl)-L-alanyloxy]-5-hydroxyindole 7.14. 3-[N-(Benzyloxycarbonyl)-L-alanyloxy]-5-methoxyindole 7.15. 3-[N-Toluene-4'-sulphonyl)-L-alanyloxy]-5-benzyloxyindole 7.16. 3-[N-(Toluene-4'-sulphonyl)-L-alanyloxy]-4-carboxyindole 7.17. 3-[N-(Toluene-4'-sulphonyl)-L-alanyloxy]-4-benzyloxycarbonyl-indole 7.18. 3-[N-(Toluene-4'-sulphonyl)-L-alanyloxy]-5-(carboxymethoxy)-indole 7.19. 3-[N-(Toluene-4'-sulphonyl)-L-alanyloxy]-5-(benzyloxycarbonyl-methoxy)-indole 7.20. 3-[N-(Toluene-4'-sulphonyl)-L-alanyloxy]-6-nitroindole 7.21. 3-[N-(Toluene-4'-sulphonyl)-L-alanyloxy]-6-acetylamino-indole 7.22. 3-[N-(Toluene-4'-sulphonyl)-L-alanyloxy]-benzo[g]-indole 7.23. 1-Methyl-3-[N-(benzyloxycarbonyl)-L-alanyloxy]-indole
colorless crystals; m.p. 92° C. $[\alpha]_D^{20} = -49.5°$, c=1% (methanol)

7.24. 1-Benzyl-3-[N-(toluene-4'-sulphonyl)-L-alanyloxy]-indole
colorless crystals; m.p. 149°-152° C. $[\alpha]_D^{20} = -54.9°$, c=1% (DMF)

7.25. 1-Phenyl-3-[N-(toluene-4'-sulphonyl)-L-alanyloxy]-indole 7.26. 1-Acetyl-3-[N-(toluene-4'-sulphonyl)-L-alanyloxy]-indole 7.27. 1-Benzoyl-3-[N-(toluene-4'-sulphonyl)-L-alanyloxy]-indole
colorless crystals; m.p. 155°-156° C. $[\alpha]_D^{20} = -54.7°$, c=1% (DMF)

7.28. 3-[N-(Benzyloxycarbonyl)-glycyloxy]-indole
colorless crystals; m.p. 122°-124° C.

7.29. 3-[N-(Toluene-4'-sulphonyl)-glycyloxy]-indole
colourless crystals; m.p. 103°-105° C.

7.30. 3-[N-(Toluene-2'-sulphonyl)-L-alanyloxy]-indole
colorless amorphous powder; $[\alpha]_D^{20} = -62.5°$, c=1% (methanol)
TLC finished plate silica gel (elution agent: toluene-dioxan 9:1 v/v, detection: UV, NH$_3$ (gas), R$_F$ value: 0.20)

7.31. 3-[N-(Toluene-3'-sulphonyl)-L-alanyloxy]-indole
colorless crystals; m.p. 94° C. $[\alpha]_D^{20} = -54.9°$, c=1% (methanol)

7.32. 3-[N-(Toluene-4'-sulphonyl)-D-alanyloxy]-indole
colorless crystals; m.p. 98° C. $[\alpha]_D^{20} = +53.1°$, c=1% (methanol).

7.33. 3-[N-(Benzyloxycarbonyl)-D,L-alanyloxy]-indole
colorless, crystals; m.p. 110°-111° C.

7.34. 3-[N-(Benzyloxycarbonyl)-L-valeryloxy]-indole
colorless crystals; m.p. 64°-65° C. $[\alpha]_D^{20} = -41.1°$, c=1% (methanol)

7.35. 3-[N-(Benzyloxycarbonyl)-L-leucyloxy]-indole
colorless crystals; m.p. 73°-75° C. $[\alpha]_D^{20} = -42.2°$, c=1% (methanol)

7.36. 3-[N-(Benzyloxycarbonyl)-L-isoleucyloxy]-indole
colorless amorphous powder; $[\alpha]_D^{20} = -30.6°$, c=1% (methanol),
TLC: finished plate silica gel (elution agent: toluene-dioxan 2:1 v/v, detection: UV, NH$_3$ (gas), R$_F$ value: 0.57).

7.37. 3-[N-(Benzyloxycarbonyl)-L-phenylalanyloxy]-indole
yellowish crystals; m.p. 125° C.
TLC: finished plate silica gel (elution agent: toluene-dioxan 9:1 v/v, detection: UV, NH$_3$ (gas), R$_F$ value: 0.56)

7.38. 3-[N-(Toluene-4'-sulphonyl)-L-phenylalanyloxy]-indole
colorless crystals; m.p. 167°-169° C. $[\alpha]_D^{20} = -34.4°$, c=1% (methanol)

7.39. 3-[N-Acetyl-L-tyrosyloxy]-indole
7.40. 3-[N-Benzoyl-L-tyrosyloxy]-indole
7.41. 3-[N-(Benzyloxycarbonyl)-L-tyrosyloxy]-indole
colorless amorphous foam
$[\alpha]_D^{20} = -22.6°$, c=1% (methanol), TLC: finished plate, silica gel (elution agent: toluene-dioxan 4:1 v/v, detection: UV, NH$_3$ (gas), RF value: 0.27)
7.42. 3-[N-(Toluene-4'-sulphonyl)-L-tyrosyloxy]-indole
colorless crystals; m.p. 171° C.
$[\alpha]_D^{20} = -28.3°$, c=1% (methanol)
7.43. 3-[N-(Toluene-4'-sulphonyl)-O-acetyl-L-tyrosyloxy]-indole
colorless crystals; m.p. 168°-170° C.
$[\alpha]_D^{20} = -24.1°$, c=1% (dimethylformamide)
7.44. 3-[N-(Benzyloxycarbonyl)-L-alanyl-L-alanyloxy]-indole
colorless crystals; m.p. 144° C.
$[\alpha]_D^{20} = -17.3°$, c=1% (methanol)
7.45. 3-[N-(Toluene-4'-sulphonyl)-D-alanyl-L-alanyloxy]-indole
yellowish, amorphous foam:
$[\alpha]_D^{20} = +5.8°$, c=1% (methanol) TLC: finished plate silica gel (elution agent: toluene-dioxan 4:1 v/v, detection: UV, NH$_3$ (gas), R$_F$ value: 0.19)
7.46. 3-[N-(Benzyloxycarbonyl)-L-alanyl-L-alanyl-L-alanyloxy]-indole
colorless crystals; m.p. 156° C.
$[\alpha]_D^{20} = -39.5°$, c=1% (methanol)
7.47. 3-[N-(Toluene-4'-sulphonyl)-D-alanyl-D-alanyl-L-alanyloxy]-indole
colorless crystals; m.p. 216° C.
$[\alpha]_D^{20} = +53.8°$, c=1% (methanol)
7.48. 3-[N-Acetyl-L-alanyloxy]-indole
colorless, amorphous foam.
$[\alpha]_D^{20} = -12.5°$, c=1% (methanol),
TLC: finished plate silica gel (elution agent: ethyl acetate-dichloromethane 10:1 v/v, detection: UV, NH$_3$ (gas), R$_F$ value: 0.33)
7.49. 3-[N-Succinyl-L-alanyloxy]-indole colorless crystals; m.p. 142° C.
$[\alpha]_D^{20} = -63.9°$, c=1% (methanol)
7.50. 3-[N-Benzoyl-D,L-alanyloxy]-indole
colorless crystals; m.p. 171° C.
7.51. 3-[N-Phthaloyl-L-alanyloxy]-indole
colorless crystals; m.p. 58° C.
$[\alpha]_D^{20} = -26.3°$, c=1% (methanol)
7.52. 3-[N-(Ethoxycarbonyl)-L-alanyloxy]-indole
colorless crystals; m.p. 96° C.
$[\alpha]_D^{20} = -68.9°$, c=1% (methanol)
7.53. 3-[N-(Cyclohexyloxycarbonyl)-L-alanyloxy]-indole
colorless crystals; m.p. 149° C.
$[\alpha]_D^{20} = -60.4°$, c=1% (methanol)
7.54. 3-[N-(Phenyloxycarbonyl)-L-alanyloxy]-indole
colorless crystals; m.p. 161° C.
$[\alpha]_D^{20} = -96.0°$, c=1% (methanol)
7.55. 3-[N-(4'-Methylbenzyloxycarbonyl)-L-alanyloxy]-indole
colorless crystals; m.p. 135° C.
$[\alpha]_D^{20} = -45.9°$, c=1% (methanol)
7.56. 3-[N-(4'-Nitrobenzyloxycarbonyl)-L-alanyloxy]-indole
yellowish crystals; m.p. 160° C.
$[\alpha]_D^{20} = -29.4°$, c=1% (methanol)
7.57. 3-[N-(Benzylthiocarbonyl)-L-alanyloxy]-indole
colorless crystals; m.p. 122° C.
$[\alpha]_D^{20} = -77.8°$, c=1% (methanol)
7.58. 3-N-(Methanesulphonyl)-L-alanyloxy]-indole
colorless crystals; m.p. 164°-166° C.
$[\alpha]_D^{20} = -54.0°$, c=1% (methanol)
7.59. 3-[N-(Benzylsulphonyl-L-alanyloxy]-indole
colorless, viscose oil
$[\alpha]_D^{20} = -54.8°$, c=1% (methanol)
TLC: finished plate silica gel, (elution agent: toluene-ethyl acetate 2:1 v/v, detection: UV, NH$_3$ (gas), R$_F$ value: 0.40)
7.60. 3-[N-(Benzenesulphonyl)-L-alanyloxy]-indole
colorless, viscose oil
$[\alpha]_D^{20} = -59.8°$, c=1% (methanol) TLC: finished plate silica gel (elution agent: toluene-ethyl acetate 2:1 v/v, detection: UV, NH$_3$ (gas), R$_F$ value: 0.48)
7.61. 3-[N-(4'-Bromobenzenesulphonyl)-L-alanyloxy]-indole
yellowish, amorphous powder
TLC: finished plate silica gel (elution agent: toluene-dioxan 4:1 v/v, detection: UV, NH$_3$ (gas), R$_F$ value: 0.39)
7.62. 3-[N-(4'-Nitrobenzenesulphonyl)-L-alanyloxy]-indole
colorless crystals; m.p. 136°-137° C.
$[\alpha]_D^{20} = -35.9°$, c=1% (methanol)
7.63. 3-[N-(4'-Acetylaminobenzenesulphonyl)-L-alanyloxy]-indole
colorless crystals; m.p. 162°-163° C.
$[\alpha]_D^{20} = -57.2°$, c=1% (methanol)
7.64. 3-[N-(4'-n-Butylbenzenesulphonyl)-L-alanyloxy]-indole
colorless crystals; m.p. 105° C.
$[\alpha]_D^{20} = -46.1°$, c=1% (methanol)
7.65. 3-[N-(4'-tert.-Butylbenzenesulphonyl)-L-alanyloxy]-indole
colorless crystals; m.p. 140° C.
$[\alpha]_D^{20} = -43.3°$, c=1% (methanol)
7.66. 3-[N-(4'-n-Octylbenzenesulphonyl)-L-alanyloxy]-indole
colorless crystals; m.p. 57° C.
$[\alpha]_D^{20} = -34.2°$, c=1% (methanol)
7.67. 3-[N-(4'-Hydroxybenzenesulphonyl)-L-alanyloxy]-indole
viscous, pale reddish oil
TLC: finished plate silica gel (elution agent: toluene-dioxan 1:1 v/v, detection: UV, NH$_3$ (gas), R$_F$ value: 0.62)
7.68. 3-[N-(4'-Methoxybenzenesulphonyl)-L-alanyloxy]-indole
colorless crystals; m.p. 126°-128° C.
$[\alpha]_D^{20} = -54.3°$, c=1% (methanol)
7.69. 3-[N-(4'-Benzyloxybenzenesulphonyl)-L-alanyloxy]-indole
colorless crystals; m.p. 112° C.
$[\alpha]_D^{20} = -40.3°$, c=1% (methanol)
7.70. 3-[N-(4'-(2''-Hydroxyethoxy)-benzenesulphonyl)-L-alanyloxy]-indole
7.71. 3-[N-(4'-(3''-Oxa-5''-hydroxy-n-pentyloxy)-benzenesulphonyl)-L-alanyloxy]-indole
colorless, viscous oil; $[\alpha]_D^{20} = -36.4°$, c=1% (methanol)
TLC: finished plate silica gel (elution agent: toluene-ethyl acetate 1:10 v/v), detection: UV, NH$_3$ (gas), R$_F$ value: 0.37
7.72. 3-[N-(4'-{3'',6''-Di-oxa-n-heptyloxy}-benzenesulphonyl)-L-alanyloxy]-indole
pale reddish viscous oil
TLC: finished plate silica gel (elution agent: toluene-dioxan 4:1 v/v, detection: UV, NH$_3$ (gas), R$_F$ value: 0.21

7.73. 3-[N-(4'-(2''-Hydroxyethyl)-benzenesulphonyl)-L-alanyloxy]-indole
yellowish, amorphous powder, $[\alpha]_D^{20} = -54.50$, c=1% (methanol); TLC: finished plate silica gel (elution agent: toluene-ethyl acetate 1:2 v/v), detection: UV, NH$_3$ (gas), R$_F$ value: 0.26

7.74. 3-[N-(4'-{2''-{{4''-Nitrobenzyloxy}}-ethyl}-benzenesulphonyl)-L-alanyloxy]-indole 7.75. 3-[N-(4'-(2''-Chloroethyl)-benzenesulphonyl)-L-alanyloxy]-indole
pale reddish, amorphous foam.
$[\alpha]_D^{20} = -48.3°$, c=1% (methanol),
TLC: finished plate silica gel (elution agent: toluene-ethyl acetate 5:1 v/v), detection: UV, NH$_3$ (gas), R$_F$ value: 0.20.

7.76. 3-[N-(4'-Cyanobenzenesulphonyl)-L-alanyloxy]-indole
colorless crystals; m.p. 131° C.
$[\alpha]_D^{20} = -47.0°$, c=1% (dimethylformamide)

7.77. 3-[N-(4'-Carboxybenzenesulphonyl)-L-alanyloxyindole
colorless crystals; m.p. 143° C.
$[\alpha]_D^{20} = -51.0°$, c=1% (methanol)

7.78. 3-[N-(4'-Benzyloxycarbonylbenzenesulphonyl)-L-alanyloxy]-indole
colorless crystals; m.p. 178° C.
$[\alpha]_D^{20} = -42.8°$, c=1% (acetone)

7.79. 3-[N-(4'-Carbamoylbenzenesulphonyl)-L-alanyloxy]-indole
colorless crystals; m.p. 206° C.
$[\alpha]_D^{20} = -58.0°$, c=1% (acetone)

7.80. 3-[N-(4'-Dimethylcarbamoyl)-benzenesulphonyl)-L-alanyloxy]-indole
colorless crystals; m.p. 170°-172° C.
$[\alpha]_D^{20} = -46.4°$, c=1% (dimethylformamide)

7.81. 3-[N-Methyl-N-(toluene-4'-sulphonyl)-L-alanyloxy]-indole
colorless crystals; m.p. 82° C.
$[\alpha]_D^{20} = -42.2°$, c=1% (methanol)

7.82. 3-[N-(2',4',6'-Trimethylbenzenesulphonyl)-L-alanyloxy]-indole
colorless crystals; m.p. 192°-194° C.
$[\alpha]_D^{20} = -63.8°$, c=1% (methanol)

7.83. 3-[N-(Biphenyl-4'-sulphonyl)-L-alanyloxy]-indole
colorless crystals; m.p. 159° C.
$[\alpha]_D^{20} = -42.0°$, c=1% (methanol)

7.84. 3-[N-(Naphthalene-2'-sulphonyl)-L-alanyloxy]-indole
pale reddish crystals; m.p. 103°-105° C.
TLC: finished plate silica gel (elution agent: toluene-dioxan 4:1 v/v), detection: UV, NH$_3$ (gas), R$_F$ value: 0.41

7.85. 3-[N-(4'-Acetylaminonaphthalene-1'-sulphonyl)-L-alanyloxy]-indole
colorless crystals; m.p. 129°-132° C.
$[\alpha]_D^{20} = -63.2°$, c=1% (methanol)

7.86. 3-[N-(5'-Dimethylaminonaphthalene-1'-sulphonyl)-L-alanyloxy]-indole
colorless crystals; m.p. 170° C.
$[\alpha]_D^{20} = -30.7°$, c=1% (methanol)

7.87. 3-[N-(Benzyloxycarbonyl)-L-alanyloxy]-benzo[b]-thiophene
colorless, viscous oil
$[\alpha]_D^{20} = -42.2°$, c=1% (methanol)
TLC: finished plate silica gel (elution agent: dichloromethane), detection: UV, NaOH/K$_3$Fe(CN)$_6$, R$_F$ value: 0.13

7.88. 3-[N-Toluene-4'-sulphonyl)-L-alanyloxy]-5-benzylindole 7.89. 3-[N-(Toluene-4'-sulphonyl)-L-alanyloxy]-5-phenylindole

EXAMPLE 8

3-[N-(tert.-Butyloxycarbonyl)-L-alanyloxy]-indole

For the reaction by the carbodiimide process, 3.23 g. (0.017 mol) N-tert.-butyloxycarbonyl-L-alanine and 2.27 g. (0.017 mol) indoxyl are dissolved in 100 ml. anhydrous dioxan-dichloromethane (1:1 v/v). After the addition of a solution of 3.87 g. (0.019 mol) dicyclohexylcarbodiimide (DCC) in 20 ml. anhydrous dioxan, the reaction mixture is stirred for 68 hours at ambient temperature, with the exclusion of water and oxygen. Precipitated N,N'-dicyclohexylurea is filtered off with suction, the solvent is distilled off in a vacuum and the residue is taken up in about 100 ml. ethyl acetate. After filtering off with suction a further amount of precipitated N,N'-dicyclohexylurea, the clear ethyl acetate solution is successively washed twice with 30 ml. amounts of 1 N aqueous citric acid solution, 20 ml. water, 50 ml. 5 to 10% aqueous sodium bicarbonate solution and 25 ml. water. After drying over anhydrous sodium sulphate, the ethyl acetate phase is evaporated in a vacuum. The amorphous residue obtained is purified by column chromatography in silica gel with a mixture of toluene and dioxan (9:1 v/v). After evaporation of the collected fractions in a vacuum and recrystallization of the residue from ethyl acetate-diethyl ether (1:10 v/v), there is obtained 1.04 g. (20% of theory) 3-[N-(tert.-butyloxycarbonyl)-L-alanyloxy]-indole in the form of colorless crystals; m.p. 158° C.; $[\alpha]_D^{20} = -65.0°$ (c=1% in methanol).

In the case of this reaction, too, as by-product there is formed the 3-hydroxyindole substituted in the 1-position (see Example 7).

In analogous manner, by the reaction of the appropriately substituted indoxyl compounds with the appropriate amino acids, there are obtained the following substrates; here, too, in all cases, as by-products there are formed the corresponding 3-hydroxyindoles substituted in the 1-position:

8.1. 3-[N-Formyl-L-alanyloxy]-indole
colorless crystals; m.p. 121°-122° C.
$[\alpha]_D^{20} = -2.5°$, c=1% (methanol)

8.2. 3-[N-(4'-Methoxybenzyloxycarbonyl)-L-alanyloxy]-indole
colorless crystals; m.p. 92° C.
$[\alpha]_D^{20} = -42.9°$, c=1% (methanol)

8.3. 3-[N-(N'-(Piperidino)-oxycarbonyl)-L-alanyloxy]-indole
colorless crystals; m.p. 104° C.
$[\alpha]_D^{20} = -24.7°$, c=1% (methanol)

8.4. 3-[N-(Thienyl-(2')-methoxycarbonyl)-L-alanyloxy]-indole
colorless crystals: m.p. 134° C.
$[\alpha]_D^{20} = -55.7°$, c=1% (methanol)

8.5. 3-[N-(Quinoline-8'-sulphonyl)-L-alanyloxy]-indole
amorphous, pale reddish powder
TLC: finished plate silica gel (elution agent: toluene-dioxan 4:1 v/v), detection: UV, NH$_3$ (gas), R$_F$ value: 0.23

8.6. 3-[N-(Diphenylcarbamoyl)-L-alanyloxy]-indole
colorless crystals; m.p. 188°-190° C.
$[\alpha]_D^{20} = +22.2°$, c=1% (pyridine)

EXAMPLE 9

3-[N-(Furyl-(2')-methoxycarbonyl)-L-alanyloxy]-indole

For the reaction by the active ester process, 4.26 g. (0.02 mol) N-(furyl-(2')-methoxycarbonyl)-L-alanine and 5.4 g. (0.04 mol) N-hydroxybenzotriazole are dissolved in 50 ml. anhydrous tetrahydrofuran (THF), cooled to 0° C. and mixed with a solution of 4.4 g. (0.022 mol) dicyclohexylcarbodiimide (DCC) in 10 ml. anhydrous THF. For the formation of the active ester, the reaction mixture is stirred for 1.5 hours at 0° C. and then for 2 hours at ambient temperature. Thereafter, with the exclusion of oxygen and water, there are added thereto 2.66 g. (0.02 mol) indoxyl and 2.77 ml. (0.04 mol) anhydrous triethylamine. The reaction mixture is stirred for 18 hours at ambient temperature. The N,N'-dicyclohexylurea formed is filtered off with suction, the solvent is distilled off in a vacuum and the residue is worked up in the manner described in Example 7. The amorphous crude product obtained is then purified by column chromatography on a silica gel column with a mixture of toluene and ethyl acetate (5:1 v/v). After evaporation of the appropriate collected fractions and recrystallization of the residue from ethyl acetate-petroleum ether (1:1 v/v), there are obtained 3.0 g. (45.7% of theory) 3-[N-(furyl-(2')-methoxycarbonyl)-L-alanyloxy]-indole in the form of colorless crystals; m.p. 129° C.: $[\alpha]_D^{20} = -51.9°$ (c = 1% in methanol).

In an analogous manner, by the reaction of the appropriately substituted amino acids or peptides with the appropriate indoxyl compounds, there are obtained the following substances:

9.1. 3-[N-(Toluene-4'-sulphonyl-L-valyloxy]-indole
colorless crystals; m.p. 125°-127° C.
$[\alpha]_D^{20} = -24.5°$, c = 1% (methanol)

9.2. 3-[N-(4'-Dimethylaminobenzenesulphonyl)-L-alanyloxy]-indole
amorphous, pale reddish powder
TLC: finished plate silica gel (elution agent: toluene-dioxan 3:1 v/v), detection: UV, $NH_3$ (gas), $R_F$ value: 0.25

9.3. 3-[N-(4'-Acetyl-benzenesulphonyl)-L-alanyloxy]-indole 9.4. 3-[N-(4'-Methoxycarbonylbenzenesulphonyl)-L-alanyloxy]-indole
colorless crystals; m.p. 140°-141° C.
$[\alpha]_D^{20} = -40.3°$, c = 1% (methanol)

9.5. 3-[N-(4'-Carboxymethylbenzenesulphonyl)-L-alanyloxy]-indole
amorphous, colorless foam
$[\alpha]_D^{20} = -82.1°$, c = 1% (methanol)
TLC: finished plate silica gel (elution agent: isopropanol-n-butyl acetate-water 5:3:2 v/v/v), detection: UV, $NH_3$ (gas), $R_F$ value: 0.68

9.6. 3-[N-(4'-Carboxymethoxybenzenesulphonyl)-L-alanyloxy]-indole
amorphous, colorless foam
$[\alpha]_D^{20} = -47.7°$, c = 1% (methanol)
TLC: finished plate silica gel (elution agent: toluene-dioxan-glacial acetic acid 6:2:1 v/v/v), detection: UV, $NH_3$ (gas), $R_F$ value: 0.27

9.7. 3-[N-(4'-Carboxymethylamino benzenesulphonyl)-L-alanyloxy]-indole
colorless crystals; m.p. 151°-153° C. (decomp.)
$[\alpha]_D^{20} = -71.5°$, c = 1% (methanol)

9.8. 3-[N'-(4'-{Benzyloxycarbonylmethylamino}-benzenesulphonyl)-L-alanyloxy]-indole
colorless crystals; m.p. 110°-113° C.
$[\alpha]_D^{20} = -60.0°$, c = 1% (methanol)

9.9. 3-[N-(4'-Fluorobenzenesulphonyl)-L-alanyloxy]-indole
colorless crystals; m.p. 94°-95° C.
$[\alpha]_D^{20} = -48.5°$, c = 1% (methanol)

9.10. 3-[N-(4'-Fluorosulphonyl-benzenesulphonyl)-L-alanyloxy]-indole 9.11. 3-[N-(4'-Sulphamoyl-benzenesulphonyl)-L-alanyloxy]-indole 9.12. 3-[N-Acetyl-N-(toluene-4'-sulphonyl)-L-alanyloxy]-indole
colorless, amorphous powder
$[\alpha]_D^{20} = -10.6°$, c = 1% (methanol)
TLC: finished plate silica gel (elution agent: toluene-dioxan 9:1 v/v) detection: UV, $NH_3$ (gas), $R_F$ value: 0.17

9.13. 3-[N-(Pyridine-3'-sulphonyl)-L-alanyloxy]-indole
colorless crystals; m.p. 155°-157° C.
$[\alpha]_D^{20} = -55.1°$, c = 1% (methanol)

9.14. 3-[N-(5',5'-Dimethyl-3'-oxocyclohexen-1'-yl)-L-alanyloxy]-indole
colorless crystals; m.p. 154° C.
$[\alpha]_D^{20} = -272.2°$, c = 1% (methanol)

9.15. 3-[N-(Di-{4'-nitrobenzyl}-phosphoryl)-L-alanyloxy]-indole 9.16. 3-[N-(Di-{4'-bromobenzyl}-phosphoryl)-L-alanyloxy]-indole 9.17. 3-[N-(toluene-4'-sulphonyl)-L-alanyloxy]-5-methoxy-indole
colorless, viscous oil
$[\alpha]_D^{20} = -46.8°$ (c = 1% in methanol);
TLC: finished plate, silica gel (elution agent: toluene-ethyl acetate (2:1 v/v)), detection: UV, $NH_3$ (gas), $R_F$ value 0.45.

EXAMPLE 10

3-[N-(3',6'-Dioxa-n-heptyloxycarbonyl)-L-alanyloxy]-indole

For the reaction according to the mixed anhydride process, 3.52 g. (0.015 mol) N-(3,6-dioxa-n-heptyloxycarbonyl)-L-alanine are dissolved in 35 ml. anhydrous tetrahydrofuran (THF). After the addition of 2.1 ml. (0.015 mol) triethylamine, the mixture is cooled to −15° C. and then, for the formation of the mixed anhydride, mixed with 1.43 ml. (0.015 mol) ethyl chloroformate. After stirring for 1 hour at −15° C., a solution of 2.00 g. (0.015 mol) indoxyl in 20 ml. anhydrous THF, cooled to −15° C., is added thereto, with the exclusion of oxygen and water. The reaction mixture is stirred for a further 2 hours at −15° C. to −20° C. and then left to stand overnight in a refrigerator. The triethylamine hydrochloride formed is filtered off with suction, the solvent is stripped off in a vacuum and the residue is worked up in the manner described in Example 7. The amorphous crude product obtained is then purified by column chromatography on silica gel, first with a mixture of methylene chloride and methanol (95:5 v/v) and then with a mixture of toluene and methyl ethyl ketone (1:2 v/v). After treating the collected fractions with active charcoal and stripping off the solvent, there is obtained 0.51 g. (9.5% of theory 3-[N-(3',6'-dioxa-n-heptyloxycarbonyl)-L-alanyloxy]-indole in the form of a colorless, viscous oil; $[\alpha]_D^{20} = -40.4°$ (c = 1% in methanol); TLC: finished plate silica gel (elution agent: toluene-methyl ethyl ketone (1:2 v/v), detection: UV, NH₃ (gas); $R_F$ value = 0.54.

In an analogous manner, by the reaction of the appropriately substituted amino acids with the appropriate indoxyl compounds, there are obtained the following compounds:

10.1. 3-[N-(2'-Nitrobenzenesulphenyl)-L-alanyloxy]-indole yellow crystals; m.p. 133°–134° C.;

$[\alpha]_D^{20} = -116.0°$ (c = 1% in methanol)

10.2. 3-[N-(1'-Methyl-2'-benzoylvinyl)-L-alanyloxy]-indole pale, reddish crystals; m.p. 130°–133° C.;

TLC: finished plate silica gel (elution agent: toluene-dioxan (4:1 v/v)), detection: UV, NH₃ (gas), $R_F$ value: 0.45.

What is claimed is:

1. In a diagnostic agent for the detection of proteolytic enzymes, comprising an absorbent carrier, a film layer, a powder mixture, a lyophilizate, a solution or a reagent tablet, containing at least one chromogen and an appropriate buffer substance, the improvement comprising at least one chromogen selected from the group consisting of indoxylamino acid esters, thioindoxylamino acid esters and peptide esters of the formula

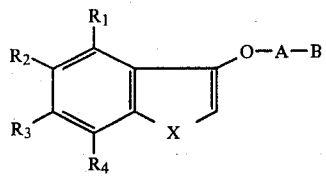

wherein $R_1$, $R_2$, $R_3$ and $R_4$ are individually selected from hydrogen, halogen, lower alkyl, lower alkoxy, aryl, aralkyl, aralkoxy, hydroxyl, carboxy, carboxy lower alkoxy, aralkoxycarbonyl, aralkyloxycarbonyl lower alkoxy, nitro or lower acylamino radicals, whereby two adjacent substituents can also represent an optionally halogenated fused benzene ring;

X is a sulfur atom or an imino group optionally substituted by a lower alkyl, aryl, aralkyl or acyl radical;

A is an amino acid or peptide residue; and

B is a nitrogen protective group.

2. Improvement as claimed in claim 1 wherein at least one conventional adjuvant is also present in said diagnostic agent.

3. Improvement as claimed in claim 2 wherein said adjuvant is at least one member selected from the group consisting of wetting agents, oxidation agents, film formers, galenical additives and strucural formers.

4. Improvement as claimed in claim 1 wherein $R_1$, $R_2$, $R_3$ and $R_4$ are hydrogen.

5. Improvement as claimed in claim 1 wherein at least one of $R_1$, $R_2$, $R_3$ and $R_4$ is halogen.

6. Improvement as claimed in claim 1 wherein at least one of $R_1$, $R_2$, $R_3$ and $R_4$ is lower alkyl.

7. Improvement as claimed in claim 1 wherein at least one of $R_1$, $R_2$, $R_3$ and $R_4$ is lower alkoxy.

8. Improvement as claimed in claim 1 wherein at least one of $R_1$, $R_2$, $R_3$, and $R_4$ is aryl or aralkyl.

9. Improvement as claimed in claim 1 wherein at least one of $R_1$, $R_2$, $R_3$ and $R_4$ is aralkoxy.

10. Improvement as claimed in claim 1 wherein at least one of $R_1$, $R_2$, $R_3$ and $R_4$ is hydroxyl.

11. Improvement as claimed in claim 1 wherein at least one of $R_1$, $R_2$, $R_3$ and $R_4$ is carboxy or carboxy lower alkoxy.

12. Improvement as claimed in claim 1 wherein at least one of $R_1$, $R_2$, $R_3$ and $R_4$ is aralkoxycarbonyl.

13. Improvement as claimed in claim 1 wherein at least one of $R_1$, $R_2$, $R_3$ and $R_4$ is aralkyloxycarbonyl lower alkoxy.

14. Improvement as claimed in claim 1 wherein at least one of $R_1$, $R_2$, $R_3$ and $R_4$ is nitro.

15. Improvement as claimed in claim 1 wherein at least one of $R_1$, $R_2$, $R_3$ and $R_4$ is lower acylamino.

16. Improvement as claimed in claim 1 wherein two adjacent radicals of $R_1$, $R_2$, $R_3$ and $R_4$ together represent a fused benzene ring or a halogenated fused benzene ring.

17. Improvement as claimed in claim 1 wherein X is sulfur.

18. Improvement as claimed in claim 1 wherein X is imino.

19. Improvement as claimed in claim 1 wherein X is substituted imino.

20. Improvement as claimed in claim 1 wherein A is an amino acid residue.

21. Improvement as claimed in claim 1 wherein A is a peptide residue.

22. Improvement as claimed in claim 1 wherein said chromogen is 3-[N-(toluene-4'-sulphonyl)-L-alanyloxy]-indole.

23. Improvement as claimed in claim 1 wherein said chromogen is 3-[N-(toluene-4'-sulphonyl)-L-alanyloxy]-4-chloro-5-bromoindole.

24. Improvement as claimed in claim 1 wherein said chromogen is 3-[N-benzoyl-D,L-alanyloxy]-indole.

25. Improvement as claimed in claim 1 wherein said chromogen is 3-[N-(benzenesulphonyl)-L-alanyloxy]-indole.

26. Improvement as claimed in claim 1 wherein said chromogen is 3-[N-(4'-n-butylbenzenesulphonyl)-L-alanyloxy]-indole.

27. Improvement as claimed in claim 1 wherein said chromogen is 3-[N-toluene-4'-sulphonyl-L-valyloxy]-indole.

28. Method of detecting proteolytic enzymes which method comprises contacting a sample suspected of containing a proteolytic enzyme with a diagnostic agent comprising an absorbent carrier, a film layer, a powder mixture, a lyophilizate, a solution or a reagent tablet, containing at least one chromogen and an appropriate buffer substance, at least one chromogen having been selected from the group consisting of indoxylamino acid esters, thioindoxylamino acid esters and peptide esters of the formula

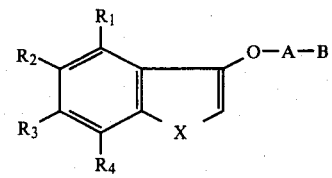

wherein $R_1$, $R_2$, $R_3$ and $R_4$ are individually selected from hydrogen, halogen, lower alkyl, lower alkoxy, aryl, aralkyl, aralkoxy, hydroxyl, carboxy, carboxy lower alkoxy, aralkoxycarbonyl, aralkyloxycarbonyl lower alkoxy, nitro or lower acylamino radicals, whereby two adjacent substituents can also represent an optionally halogenated fused benzene ring;

X is a sulfur atom or an imino group optionally substituted by a lower alkyl, aryl, aralkyl or acyl radical;
A is an amino acid or peptide residue; and
B is a nitrogen protective group.

* * * * *

UNITED STATES PATENT AND TRADEMARK OFFICE
CERTIFICATE OF CORRECTION

PATENT NO. : 4,278,763
DATED : Jul. 14, 1981
INVENTOR(S) : Dieter Berger et al

It is certified that error appears in the above-identified patent and that said Letters Patent are hereby corrected as shown below:

Title Page Priority     Delete "Dec. 30" and insert --Dec. 20--.

Signed and Sealed this

Twelfth Day of January 1982

[SEAL]

Attest:

Attesting Officer

GERALD J. MOSSINGHOFF

Commissioner of Patents and Trademarks